United States Patent [19]
Schu et al.

[11] Patent Number: 5,973,968
[45] Date of Patent: Oct. 26, 1999

[54] APPARATUS AND METHOD FOR WRITE PROTECTING A PROGRAMMABLE MEMORY

[75] Inventors: Carl Schu, Brooklyn Park; James H. Ericksen, Roseville, both of Minn.

[73] Assignee: Medtronic, Inc., Minneapolis, Minn.

[21] Appl. No.: 09/070,710

[22] Filed: Apr. 30, 1998

[51] Int. Cl.⁶ ................................................ G11C 7/00
[52] U.S. Cl. ........................................ 365/195; 365/228
[58] Field of Search ................................. 365/195, 228

[56] References Cited

U.S. PATENT DOCUMENTS

| | | | |
|---|---|---|---|
| 4,375,817 | 3/1983 | Engle et al. | 128/419 D |
| 4,379,459 | 4/1983 | Stein | 128/419 PG |
| 4,384,585 | 5/1983 | Zipes | 128/419 D |
| 4,476,868 | 10/1984 | Thompson | 128/419 PG |
| 4,548,209 | 10/1985 | Wielders et al. | 128/419 D |
| 4,556,063 | 12/1985 | Thompson et al. | 128/419 PT |
| 4,577,633 | 3/1986 | Berkovits et al. | 128/419 PG |
| 4,587,970 | 5/1986 | Holley et al. | 128/419 PG |
| 4,693,253 | 9/1987 | Adams | 128/419 D |
| 4,726,380 | 2/1988 | Vollmann et al. | 128/419 PG |
| 4,821,723 | 4/1989 | Baker, Jr. et al. | 128/419 D |
| 4,830,006 | 5/1989 | Haluska et al. | 128/419 PG |
| 4,880,005 | 11/1989 | Pless et al. | 128/419 PG |
| 4,897,819 | 1/1990 | Takizawa | 365/230.06 |
| 4,949,719 | 8/1990 | Pless et al. | 128/419 D |
| 4,949,730 | 8/1990 | Cobben et al. | 128/775 |
| 5,119,336 | 6/1992 | Itoh | 365/195 |
| 5,131,388 | 7/1992 | Pless et al. | 128/419 D |
| 5,144,949 | 9/1992 | Olson | 128/419 PG |
| 5,158,078 | 10/1992 | Bennett et al. | 128/419 PG |
| 5,188,105 | 2/1993 | Keimel | 128/419 D |
| 5,199,428 | 4/1993 | Obel et al. | 128/419 C |
| 5,207,218 | 5/1993 | Carpentier et al. | 128/419 PG |
| 5,312,453 | 5/1994 | Shelton et al. | 607/19 |
| 5,314,430 | 5/1994 | Bardy | 607/5 |
| 5,330,507 | 7/1994 | Schwartz | 607/14 |
| 5,331,966 | 7/1994 | Bennett et al. | 128/696 |
| 5,341,494 | 8/1994 | Thayer et al. | 395/425 |
| 5,354,316 | 10/1994 | Keimel | 607/15 |
| 5,447,519 | 9/1995 | Peterson | 607/5 |
| 5,545,186 | 8/1996 | Olson et al. | 607/14 |
| 5,890,199 | 3/1999 | Downs | 365/195 X |

*Primary Examiner*—Do Hyun Yoo
*Attorney, Agent, or Firm*—Thomas F. Woods; Harold R. Patton

[57] ABSTRACT

An apparatus and method for protecting memory content of a programmable memory is disclosed. A programmable memory, such as a random access memory (RAM), is configured to include a write protected portion defined as part of the programmable memory. The write protected memory portion may be configured within the memory space of a single programmable memory, or implemented in a logically or physically separate programmable memory. A microprocessor is coupled to the programmable memory and generates an access code for providing write access to the write protected portion of the programmable memory. A logic circuit, coupled to the programmable memory and microprocessor verifies the access code received from the microprocessor. In response to a verified access code, the logic circuit enables write access to the write protected portion of the programmable memory. In response to an unverified access code, the logic circuit disables write access to the write protected portion of the programmable memory. A timer may be employed to disable write access to the protected memory portion. A power on reset strategy may be employed to reset the logic circuit so as to disable write access to the protected memory portion after reestablishing power following an intended or unintended loss of power. Power may advantageously be applied and removed from the logic circuit and other system components without compromising the integrity of the programs and data stored in the write protected portion of the programmable memory.

36 Claims, 7 Drawing Sheets

APPARATUS AND METHOD FOR WRITE PROTECTING A PROGRAMMABLE MEMORY

FIELD OF THE INVENTION

The present invention relates generally to memory devices and memory access methods. More particularly, the present invention pertains to an apparatus and method for write protecting a random access memory particularly useful when incorporating such a memory in an implantable medical device.

BACKGROUND OF THE INVENTION

Various approaches have been developed to address the problem of inadvertent destruction of data stored in a programmable memory. A number of these approaches are directed to protecting against the destruction of data stored in a programmable memory due to uncontrolled operations or malfunctions occurring in a memory writing unit. A conventional approach to implementing such a memory protection scheme involves deployment of redundant circuit elements, such as redundant decoders or flip-flop circuits, to detect the presence of a spurious memory write command. U.S. Pat. No. 4,897,819 to Takizawa et al. and U.S. Pat. No. 5,119,336 to Itoh, are examples of conventional memory protection approaches that employ such redundant circuit elements.

Microprocessors and programmable memory devices are widely used in medical devices which are implanted in the human body in their intended use. It is well understood in the art that the size and power consumption of such medical devices are two parameters that are severely restricted when designing a device which is to be implanted in the body. Another parameter of paramount important is the integrity of programs and data stored in one or more programmable memories of the implantable medical device.

In most implantable medical device applications, size and power consumption considerations are of primary concern, while memory access speed is of secondary importance. A traditional approach to protecting a programmable memory using redundant write signal testing circuitry, although generally providing for decreased memory access time, typically results in a design having increased power consumption and physical memory size requirements. Such prior art memory protection schemes have limited usefulness in applications in which a reduction in memory circuitry size and power consumption is required or desired, such as in medical device applications.

Various implementations of systems and approaches for protecting a programmable memory device are known in the art, some examples of which may be found in the issued U.S. Patents listed in Table 1 below.

TABLE 1

| U.S. Pat. No. | Inventor(s) | Issue Date |
| --- | --- | --- |
| 4,897,819 | Takizawa et al. | Jan. 30, 1990 |
| 5,119,336 | Itoh | Jun. 2, 1992 |
| 5,341,494 | Thayer et al. | Aug. 23, 1994 |

All patents listed in Table 1 hereinabove are hereby incorporated by reference herein in their respective entireties. As those of ordinary skill in the art will appreciate readily upon reading the Summary of the Invention, the Detailed Description of the Various Embodiments, and the claims set forth below, many of the devices and methods disclosed in the patents of Table 1 may be modified advantageously by using the teachings of the present invention.

SUMMARY OF THE INVENTION

The present invention has certain objects. That is, various embodiments of the present invention provide solutions to one or more problems existing in the prior art with respect to programmable memory devices used with implantable medical devices. Such problems include, for example, redundancy of write signal testing circuitry, increased size of the programmable memory and ancillary circuitry, complex write signal testing strategies that increase the probability of failure, increased power consumption, and reduced reliability resulting from increased complexity of write signal testing circuitry and ancillary memory circuitry. Various embodiments of the present invention have the object of solving at least one of the foregoing problems. While some systems have been able to solve the general problem of protecting a programmable memory, such approaches have generally resulted in implementations that increase power usage and packaging size, and require deployment of complex write signal testing schemes. It is therefore another object of the present invention to provide an improved assembly and methodology for protecting a programmable memory that fulfills at least one of the foregoing objects.

In comparison to known implementations of a programmable memory protection scheme, various embodiments of the present invention may provide one or more of the following advantages: reducing the power required by circuitry that provides for the protection of a programmable memory; reducing the size of the circuitry that provides for the protection of a programmable memory; increasing the reliability of an implantable medical device that employs a microprocessor and programmable memory; increasing the integrity of programs and data stored in a programmable memory; and simplifying write signal test circuitry implemented to protect programs and data stored in a programmable memory.

Some embodiments of the invention include one or more of the following features: configuring a programmable memory to include a write protected portion thereof; generating an access code for providing access to a write protected portion of a programmable memory; a logic circuit that verifies an access code to a write protected portion of memory; enabling write access to the protected portion of a programmable memory only upon verification of a write access code; disabling write access to the protected portion of a programmable memory upon failure to verify a write access code; a verification register that receives an access code and verifies that the access code data conforms to a pre-established data pattern; a timer circuit that, upon expiration of a pre-established timeout period, generates a reset signal to disable write access to the write protected portion of a programmable memory; a power-on-reset strategy that resets write access logic circuitry so as to disable write access to the protected memory portion after reestablishing power following an intended or unintended loss of power; and selectively applying and removing power to and from write access logic circuitry and other system components without compromising the integrity of programs and data stored in the write protected portion of the programmable memory.

The above summary of the present invention is not intended to describe each embodiment or every implementation of the present invention. Advantages and attainments, together with a more complete understanding of the

Figure 1:
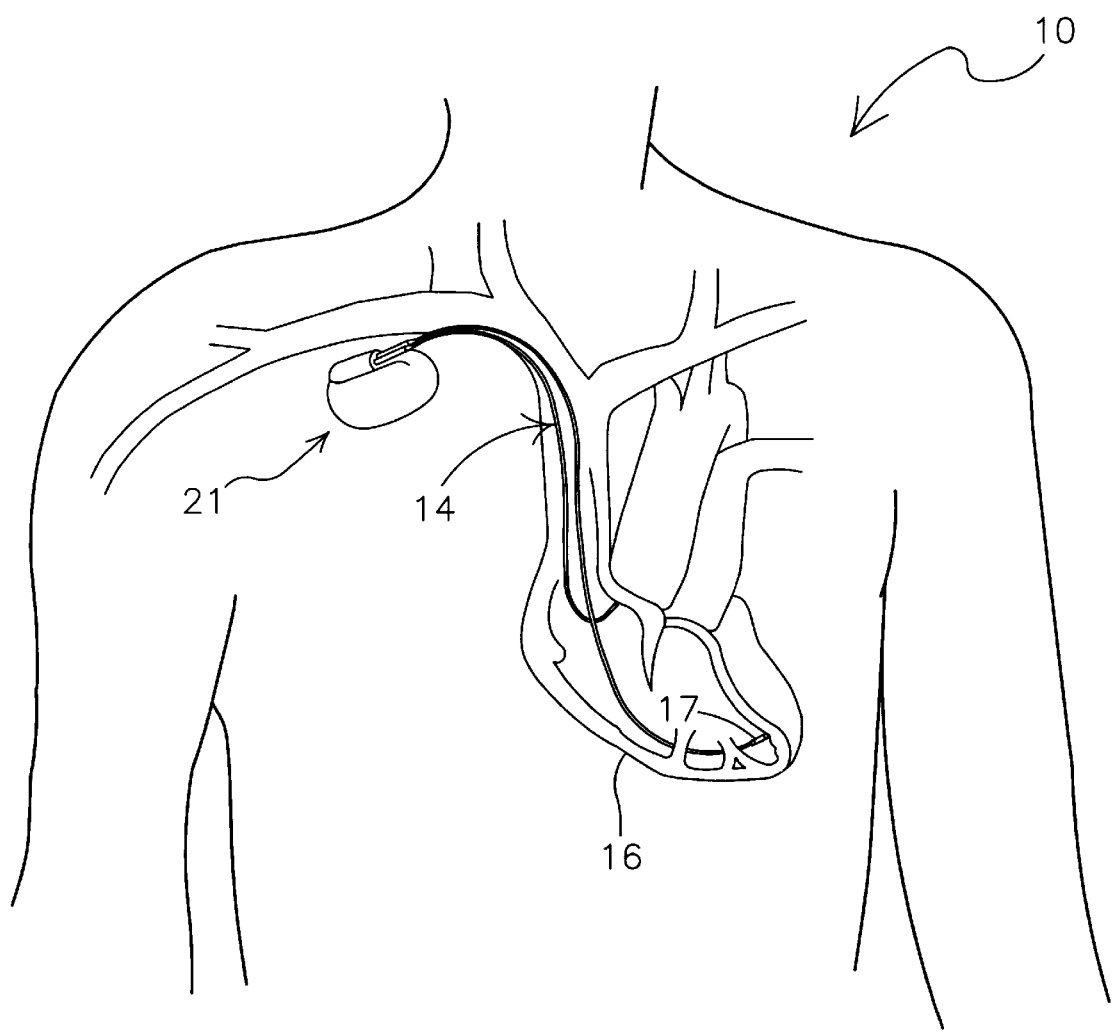
FIG. 1 shows an implantable medical device incorporating a microprocessor and write protected programmable memory in accordance with an embodiment of the present invention implanted in a human body.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the spirit and scope of the invention as defined by the appended claims.

DETAILED DESCRIPTION OF THE EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

FIG. 1 is a simplified schematic view of a medical device 21 implanted in a human body 10. A programmable memory write protection apparatus and access methodology according to the present invention is incorporated in the microprocessor based medical device 21 shown implanted in a human heart 16. It is understood that a programmable memory protection methodology according to the present invention may be implemented in a wide variety of programmable memory technologies, including, but not limited to, static RAM, dynamic RAM, and EEPROM (Electrically Erasable Programmable Read Only Memory). The objects and features of the present invention will be described herein generally within the context of random access memory (i.e., RAM). It is to be understood that other types of programmable memories may be utilized without departing from the scope of the present invention.

Controlling write access to a protected portion of a programmable memory in a manner consistent with the principles of the present invention may significantly increase the reliability of a microprocessor based medical device 21 by preventing unintended access to, and inadvertent alteration of, one or more programs and data residing in the protected portion of the memory. A conventional memory access scheme, in contrast, is generally incapable of providing the high level of program and data integrity that is realizable by employment of a write access apparatus and methodology according to the principles of the present invention without a significant and generally unacceptable increase in size and power consumption.

The traditional approach to protecting a memory by relying on redundant write signal testing circuitry, as discussed previously, generally provides for decreased memory access time, but only at the cost of increased power consumption and physical memory size. In many medical device applications, memory access speed is of secondary importance relative to size and power consumption considerations. The size of the components and circuitry incorporated in an implantable medical device, as well as the power requirements of such components and circuitry, are generally severely restricted.

The integrity of executable program software and other critical data stored in one or more of the programmable memories of an implantable medical device is also of paramount importance. In one embodiment of the present invention, a timer may be employed to disable write access to the protected memory portion after expiration of a predetermined period of time. In accordance with another embodiment, a power-on-reset strategy may be employed to reset write access logic circuitry so as to disable write access to the protected memory portion after reestablishing power following an intended or unintended loss of power. As such, power may advantageously be applied and removed from the logic circuit and other system components without compromising the integrity of the programs and data stored in the write protected portion of the programmable memory.

The simple yet elegant methodology for restricting write access to the programmable memory of a microprocessor based, implantable medical device in accordance with the principles of the present invention provides for increased reliability, a reduced packaging size, and reduced power consumption, three advantages which are of particular importance in medical device applications.

It will be appreciated that a programmable memory access and protection apparatus and methodology according to the present invention may be implemented in a wide variety of microprocessor based, implantable medical devices. In the case where the implanted medical device 21 shown in FIG. 1 is a pacemaker, one of the conductors of lead 14 is typically connected between the heart 16 and the implantable medical device 21. The medical device 21 typically includes a microprocessor and write protected RAM in accordance with the present invention to coordinate the operation of the pacemaker. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described below. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed in conjunction with the write access apparatus and method for protecting a RAM according to the present invention.

Alternatively, the medical device 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. The present invention is believed to find wide application to any form of implantable electrical device that utilizes a microprocessor to coordinate storing of information in, and write access to, a random access memory, and the present invention is believed to be particularly advantageous in those contexts where a low power consumption design is employed or desired.

In general, the implantable medical device 21 shown in FIG. 1 includes a hermetically-sealed enclosure that may include various elements, such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, in addition to other elements.

Figure 2A:
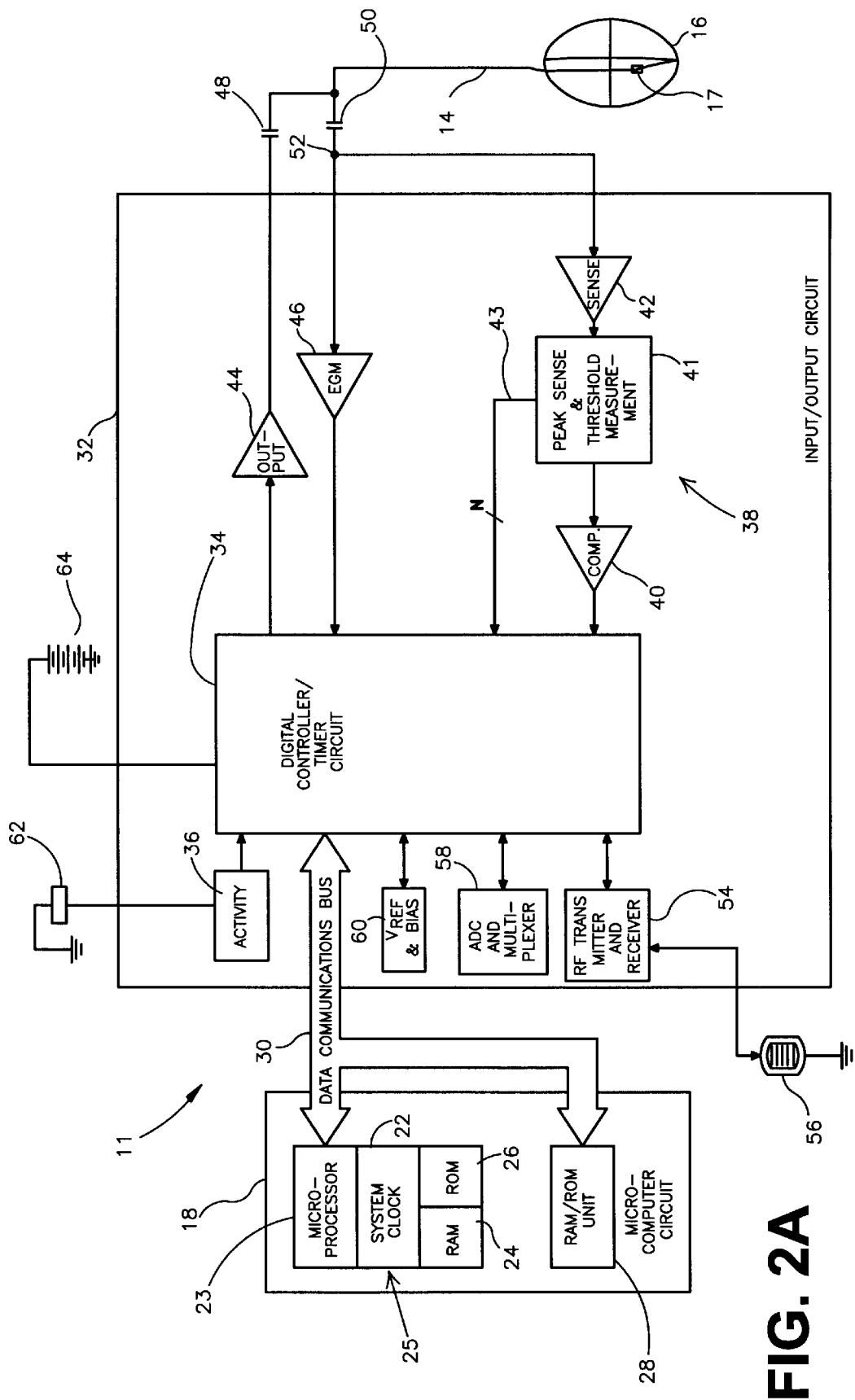
FIG. 2A shows an implantable pacemaker device incorporating a microprocessor and write protected programmable memory in accordance with one embodiment of the present invention.

FIG. 2A is a block diagram illustrating various components of a pacemaker 11 which represents one of many implantable medical devices that may benefit from incorporating a RAM protection approach of the present invention. In one embodiment, the pacemaker 11 is programmable by means of an external programming unit (not shown). One such programmer suitable for the purposes of the present invention is the commercially available Medtronic Model 9790 programmer. The programmer is a microprocessor device which provides a series of encoded signals to pacemaker 11 by means of a programming head which transmits radio frequency (RF) encoded signals to pacemaker 11 according to a telemetry system such as that described in U.S. Pat. No. 5,312,453 to Wyborny et al., the disclosure of which is hereby incorporated by reference herein in its entirety. It is to be understood, however, that the programming methodology disclosed in the Wyborny et al. patent is identified herein for illustrative purposes only and that any programming methodology may be employed so long as the desired information is transmitted to and from the pacemaker 11. One of skill in the art may choose from any of a number of available programming techniques to accomplish this task.

Pacemaker 11, illustratively shown in FIG. 2A, is electrically coupled to the patient's heart 16 by lead 14. Lead 14, which includes two conductors, is coupled to a node 52 in the circuitry of pacemaker 11 through input capacitor 50. In the presently disclosed embodiment, an activity sensor 62 provides a sensor output to a processing/amplifying activity circuit 36 of input/output circuit 32. Input/output circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 23, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34.

The electrical components shown in FIG. 2A are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blinking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40.

Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patient's heart 16 through coupling capacitor 48 in response to a pacing trigger signal provided by digital controller/timer circuit 34. For example, each time the escape interval times out, an externally transmitted pacing command is received, or such commands are received in response to other stored commands as is well known in pacing art. Output amplifier 44, for example, may correspond generally to the output amplifier disclosed in U.S. Pat. No. 4,476,868 to Thompson, also incorporated by reference herein in its entirety.

Figure 2B:
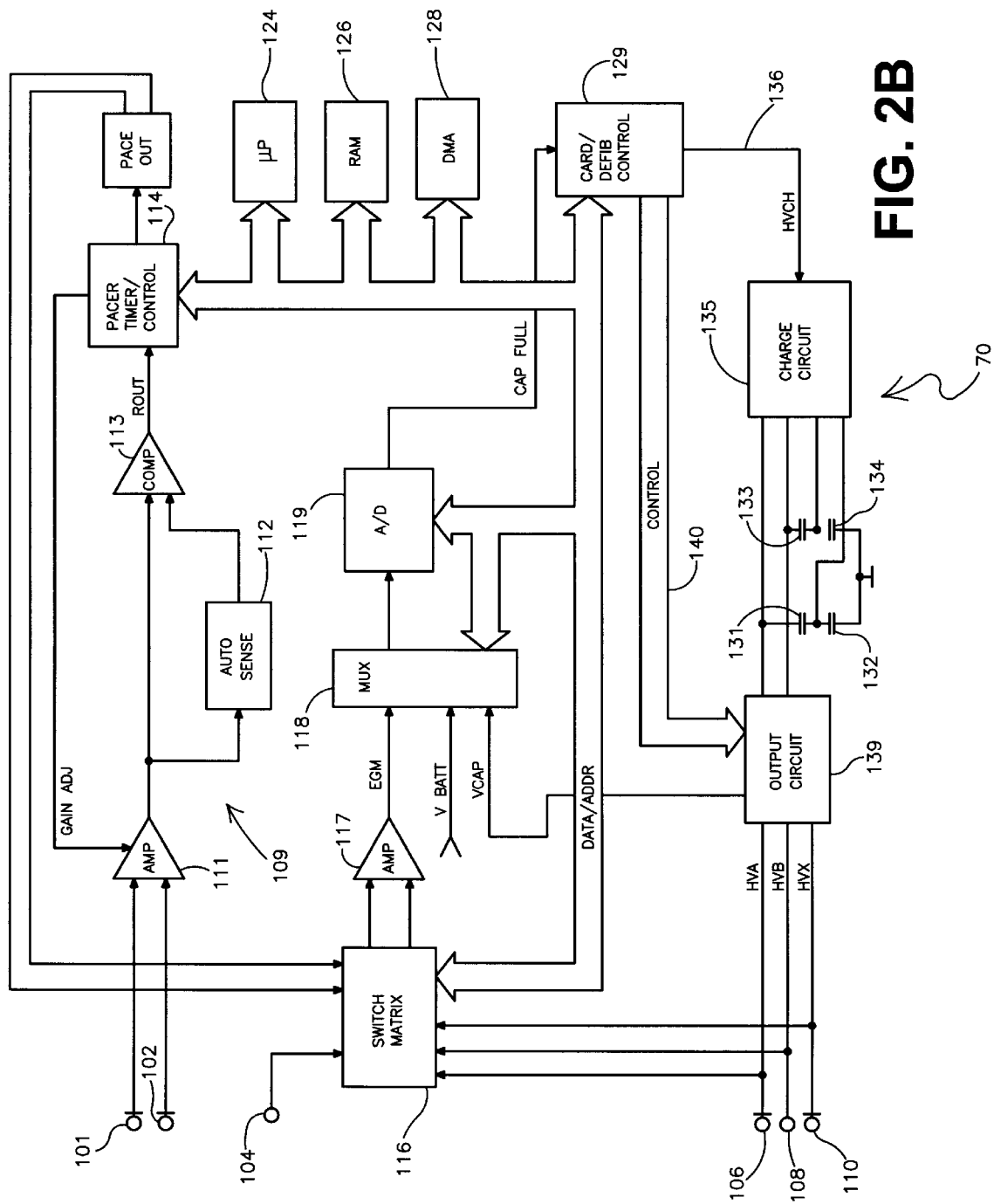
FIG. 2B shows one illustrative embodiment of a pacemaker/cardioverter/defibrillator unit incorporating a microprocessor and write protected programmable memory in accordance with another embodiment of the present invention.

FIG. 2B is a functional schematic diagram from U.S. Pat. No. 5,447,519 to Peterson which shows an implantable pacemaker/cardioverter/defibrillator (PCD) 70 which represents another one of many implantable medical devices that may utilize a write access RAM protection apparatus and methodology in accordance with the principles of the present invention. U.S. Pat. No. 5,447,519 is incorporated by reference herein in its entirety. It is understood that this diagram is an illustration of an exemplary type of device in which the invention may find application, and is not intended to limit the scope of the present invention.

Other implantable medical devices, such as those described previously, having functional organizations wherein the present invention may be useful, may also be modified to incorporate a write access RAM protection apparatus and methodology in accordance with the present invention. For example, the present invention is also believed to be useful in conjunction with implantable pacemakers/cardioverters/defibrillators as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/fibrillation discrimination function. Far field EGM signals from the selected electrodes are passed through band pass amplifier 117 and into multiplexer 118, where they are converted to multi-bit digital data signals by A/D converter 119 for storage in random access memory 126 under the control of direct memory address circuitry 128.

The processor 124 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 70 of FIG. 2B is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Further, known circuitry for controlling the timing and generation of anti-tachycardia pacing pulses is described in U.S. Pat. No. 4,577,633 to Berkovits et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Selection of a particular electrode configuration for delivery of the cardioversion or defibrillation pulses is controlled via output circuit 139 under the control of cardioversion/defibrillation control circuit 129 via control bus 140. Output circuit 139 determines which of the high voltage electrodes 106, 108 and 110 is to be employed in delivering the defibrillation or cardioversion pulse regimen.

Figure 3:
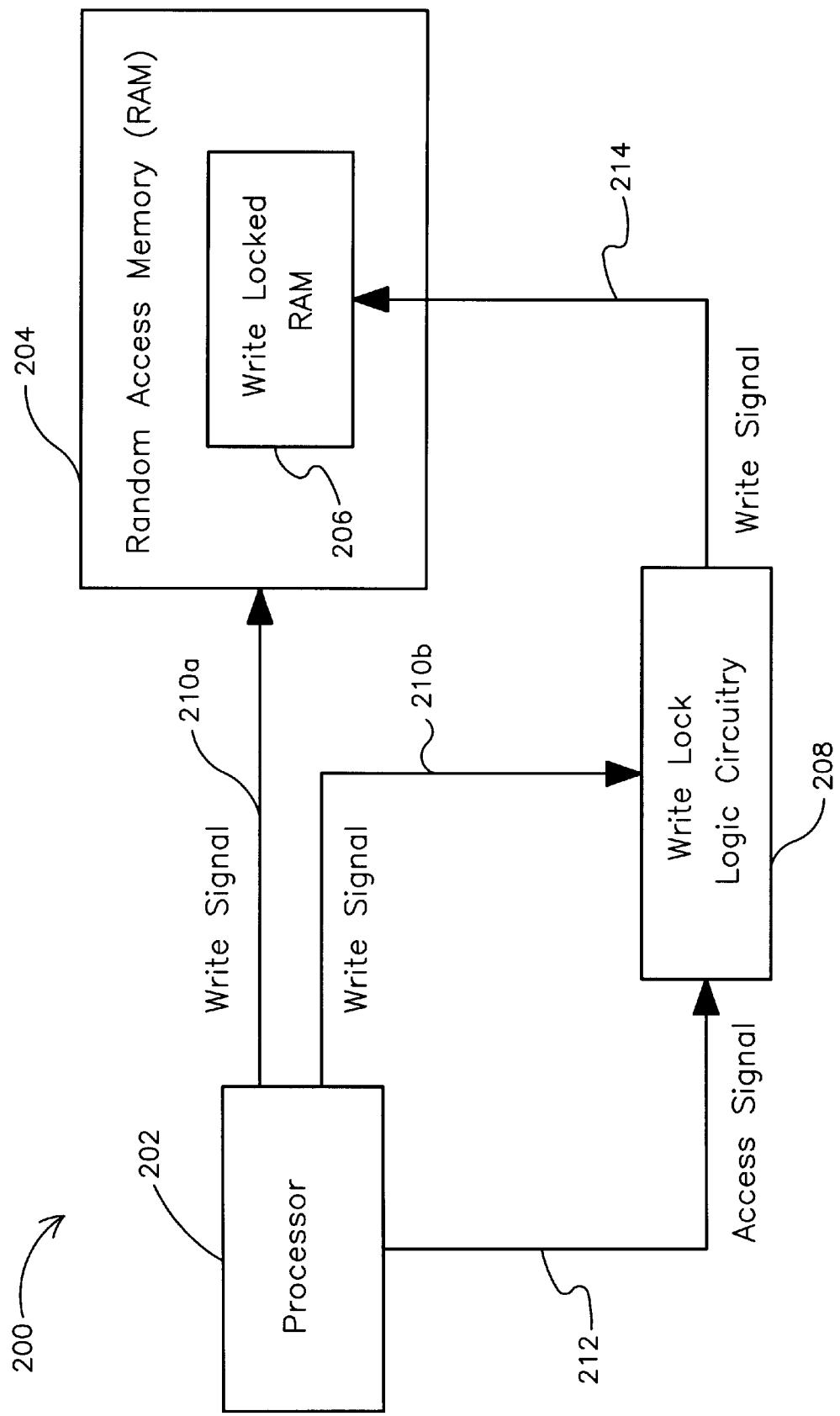
FIG. 3 shows a system block diagram of a write-protected random access memory (RAM) system architecture in accordance with an embodiment of the present invention.

FIG. 3 shows a block diagram of a system architecture for protecting a portion of random access memory in accordance with one embodiment of the present invention. A system and methodology for controlling access to a designated portion of random access memory is particularly well-suited for incorporation in a medical device, such as those described hereinabove and in the various patents incorporated herein by reference. The processor-based system 200 includes a processor 202, such as a microprocessor or programmable controller, which is coupled to a RAM 204 and to write lock logic circuitry 208. RAM 204 is configured to include a portion 206 of memory 204 in which write access is controlled by employment of a write lock methodology in accordance with the principles of the present invention. The protected portion 206 of RAM 204 is alternatively referred to herein as write lock RAM 206.

Write lock RAM 206 is generally used to store executable program software and other programs and data of high criticality. By way of example, write lock RAM 206 may be used to securely store an executable program which, when implemented by processor 202, coordinates the activities of a pacemaker, PCD or other implantable medical device. A RAM memory 204 controlled in accordance with the principles of the present invention protects sensitive program code and data from unintended alteration or corruption by internal or external hardware and/or software.

Figure 4:
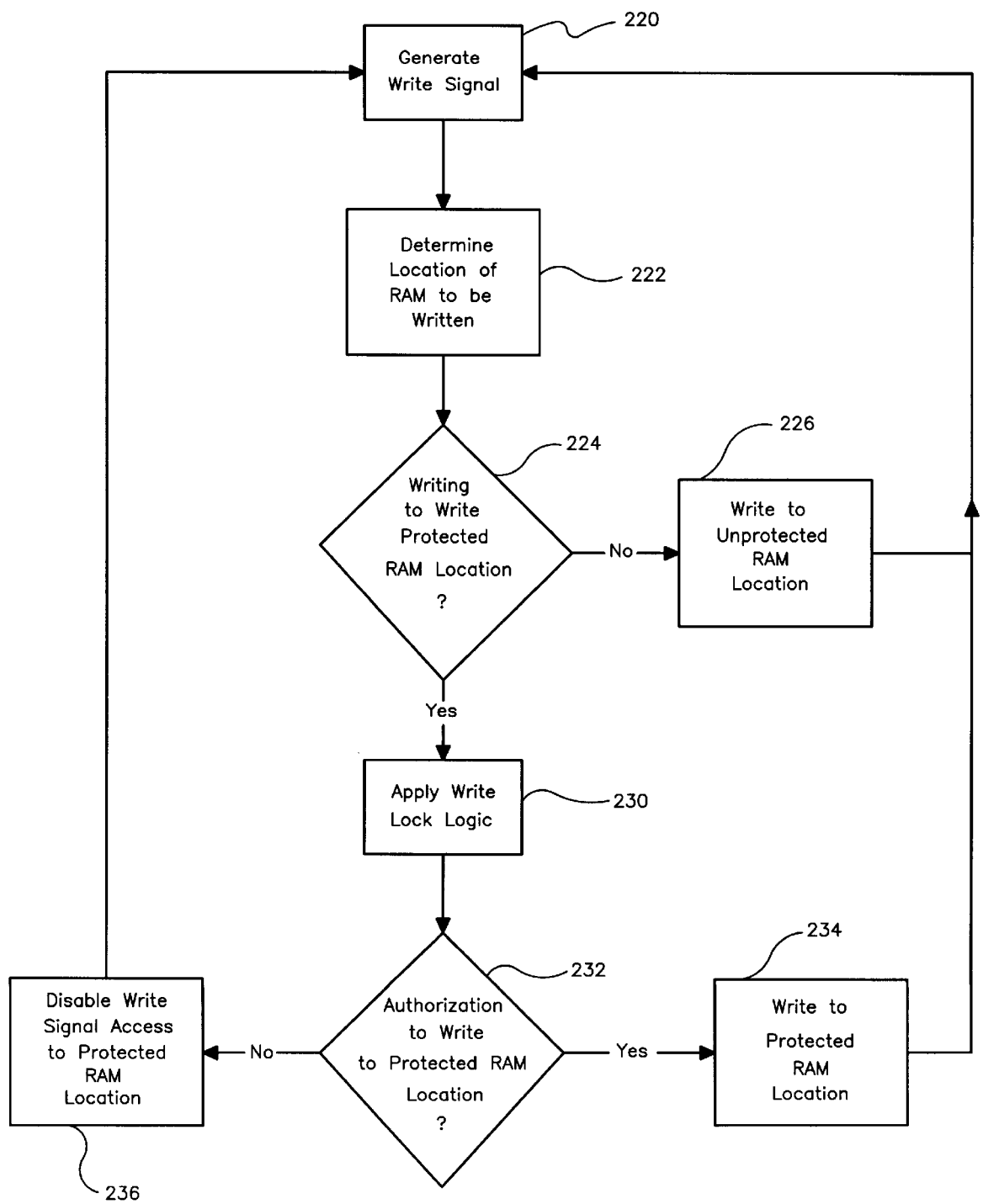
FIG. 4 shows a flow diagram from various process steps associated with enabling and disabling write access to a protected portion of RAM.

In accordance with one embodiment of the present invention, and with reference to FIGS. 3 and 4, processor 202 generates a write signal when coordinating writing of data to RAM 204. It is noted that the illustrative block diagram shown in FIG. 3 excludes address and data line connections between processor 202, RAM 204, and write lock logic circuitry 208 for purposes of clarity. Processor 202 may generate write signal 210a to effect storing of data in RAM 204 or may generate write signal 210b for writing to write lock RAM 206. It is understood that write signal 210b may represent a write signal purposefully generated by processor 202 or another component for gaining write access to write lock RAM 206. Write signal 210b may also represent an errant or unintended write signal which, if left unimpeded, would provide unauthorized write access to write lock RAM 206 that could result in potentially catastrophic alteration of sensitive program software and other critical data stored within write lock RAM 206.

Processor 202 is typically used to configure RAM 204 so as to define a write lock RAM 206 having a specified size. In one embodiment, the processor 202 allocates a contiguous block of RAM 204 memory space for purposes of supporting write lock RAM 206. It is understood that write lock RAM 206 need not be defined as a contiguous block of RAM 204 memory space, but may instead be configured to include non-contiguous RAM 204 memory space. Designating a contiguous range of RAM 204 memory address space to support write lock RAM 206 is believed to simplify implementation of a RAM memory protection methodology in accordance with the principles of the present invention.

Processor 202 generates 220 a write signal 210a or 210b when attempting to write data to RAM 204. Decoding logic is typically employed internal to or external of processor 202 to determine 222 the location in RAM 204 to which particular data is to be written. If write signal 210a indicates that write access to an unprotected location in RAM 204 is requested 224, processor 202 effects a transfer of data 226 to the unprotected RAM 204 location. It is understood that the term unprotected RAM refers to RAM storage space that is not subject to write access protection in accordance with the principles of the present invention. If processor 202 produces write signal 210b, which indicates that write access to write lock RAM 206 is required 224, write lock logic circuitry 208 operates on write signal 210b to ensure that write access to write lock RAM 206 is authorized. It is noted that the write lock logic executed by write lock circuitry 208 may be implemented as part of processor 202 in hardware and/or software, or implemented in a separate component coupled to processor 202 in hardware and/or software.

In response to write signal 210b, write lock logic is applied 230 by logic circuitry 208 in order to verify the appropriateness of providing write access to write lock RAM 206. If, after application of the write lock logic 230, write access to write lock RAM 206 is authorized 232, data is written 234 to the appropriate address locations in write lock RAM 206. If write lock logic circuitry 208 determines that write access to write lock RAM 206 is not authorized 232, write lock logic circuitry 208 prevents write signal 210b from effecting write access to write lock RAM 206. A memory fault condition typically arises upon failure to authorize write access to write lock RAM 206 in response to an errant write signal 210b generated by processor 202 or other direct memory addressing component. The fault condition is typically indicated in system memory by a latched fault bit or byte in a fault status register of processor 202.

Figure 5:
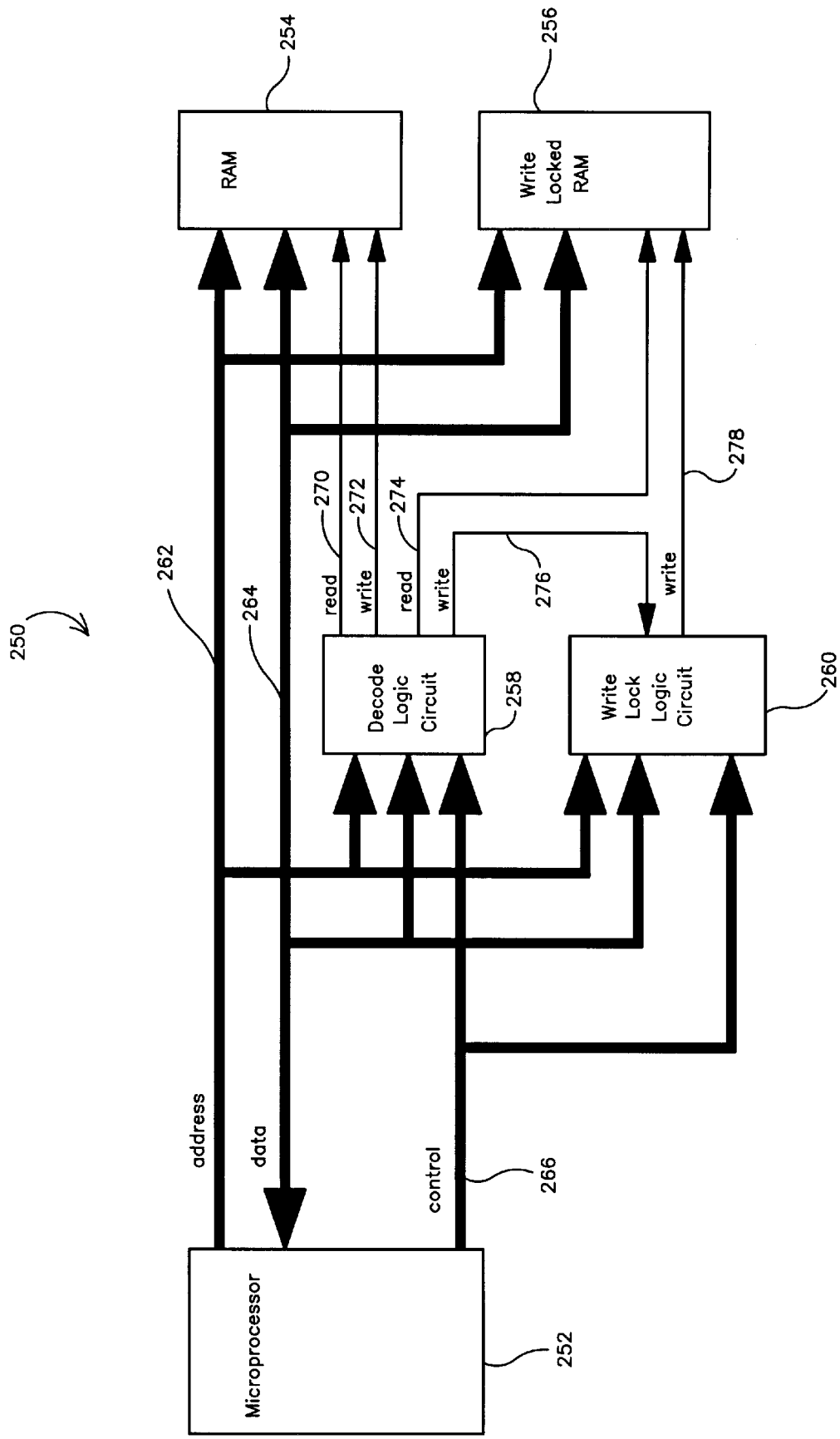
FIG. 5 shows a block diagram of a system architecture for restricting write access to a RAM in accordance with an embodiment of the present invention.

FIG. 5 shows a block diagram of another system architecture which implements a write lock methodology for protecting a random access memory from unintended write access in accordance with a further embodiment of the present invention. In the embodiment shown in FIG. 5, RAM 254 and write lock RAM 256 are shown as two separate memory devices. In the embodiment shown in FIG. 3, in contrast, write lock RAM 206 is shown as constituting a partitioned portion or portions of RAM 204. It is understood that a write lock portion of RAM within the context of the present invention may be implemented in a single RAM device or in one or more logically or physically separate RAM devices.

In the embodiment shown in FIG. 5, microprocessor 252 is coupled to RAM 254 and write lock RAM 256 via address lines 262 and data lines 264. Microprocessor 252 is also coupled to decode logic circuit 258 and write lock logic circuit 260 via address and data lines 262, 264. Decode logic circuit 258 receives control signals from microprocessor 252 via control lines 266. Control lines 266 also couple microprocessor 252 to write lock logic circuit 260. Read and write control lines 270, 272 couple decode logic circuit 258 to RAM 254. Control signals produced by microprocessor 252 are transferred to decode logical circuit 258 over control lines 266 to enable writing and reading of data to and from RAM 254. It can be further seen from FIG. 5 that microprocessor 252 may effect reading of information from write lock RAM 256 by transmitting appropriate control signals to decode logic circuit 252 via control lines 266. Decode logic circuit 258 enables reading of write lock RAM 256 contents via read line 274.

Unlike conventional RAM access schemes, write line 276 extending from decode logic circuit 258 is coupled to write lock logic circuit 260, rather than directly to RAM 254/256. Write line 278 couples write lock logic circuit 260 to write locked RAM 256. In this configuration, all requests by microprocessor 252, or other devices having direct memory access capability, to gain write access to write lock RAM 256 are further processed by write lock logic circuit 260. In response to a write signal on write line 276, write lock logic circuit 260 initiates write lock logic to verify that write access to write locked RAM 256 is permitted.

The write lock logic embodied in write lock logic circuit 260 may be implemented in a number of ways, either in hardware, software, or a combination of hardware and software. In general, the greater the number of error conditions that the write lock logic addresses, the lower the chance that accidental alteration of write lock RAM content will occur.

In accordance with one embodiment, write lock logic circuit 260 includes one or more validation registers that microprocessor 252 must write to with a specific data pattern in order to enable a write signal on write line 278. If microprocessor 252 writes a data pattern other than the pre-established data pattern into the validation registers, write lock logic circuit 260 disables transmission of a write signal over write line 278. If microprocessor 252 writes a data pattern to the validation registers that matches the pre-established data pattern, write lock logic circuit 260 enables write line 278, thereby providing write access to appropriate address locations in write lock RAM 256.

In accordance with another embodiment, a timer is employed by write lock logic circuit 260 or microprocessor 252 which, upon expiration of a pre-established period of time, resets the validation registers to a state in which write signal line 278 is disabled.

In accordance with a further embodiment, a power-on-reset strategy is employed to reset write lock logic circuit 260 so as to disable write access to write locked RAM 256 after reestablishing power following an intended or unintended loss of power. As such, power may advantageously be applied and removed from the write lock logic circuit 260 and other components coupled thereto without compromising the integrity of the programs and data stored in the write locked RAM 256. When power is restored, write lock logic circuit 260 generates a power-on-reset signal which resets the validation registers to a state such that write signal line 278 is disabled. The capability to selectively apply and remove power to and from write lock logic circuit 260, decode logic circuit 258, and other system components, including RAM 254 and write locked RAM 256, without comprising the integrity of the information stored in the write locked RAM 256 is considered to represent a significant advantage, particularly in low power applications.

Figure 6:
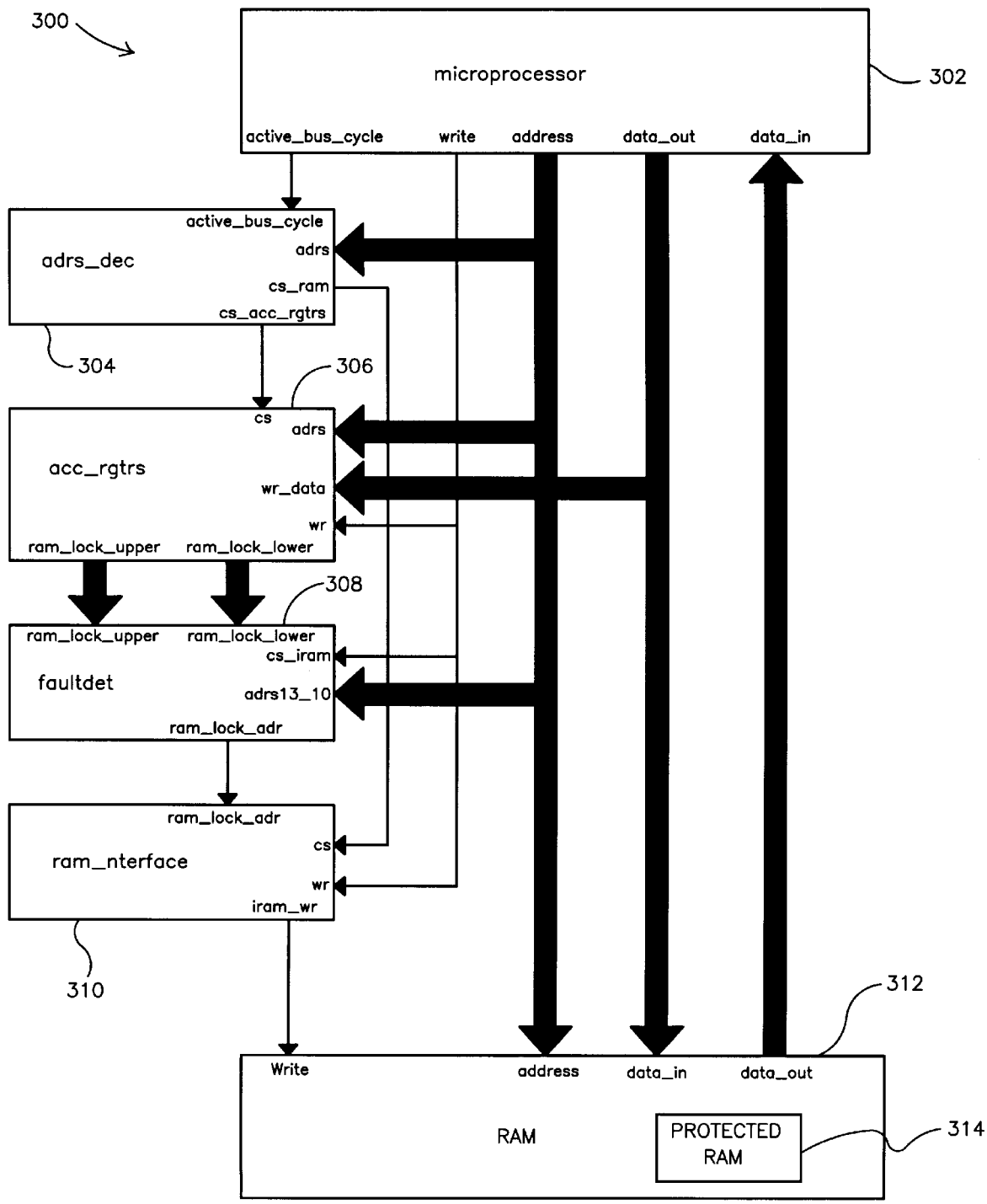
FIG. 6 shows a block diagram of a system architecture for restricting write access to a RAM in accordance with another embodiment of the present invention.

FIG. 6 shows a block diagram of a system architecture that implements a write access protection methodology for a programmable memory in accordance with another embodiment of the present invention. The system architecture 300 shown in FIG. 6 includes microprocessor 302 coupled to RAM 312 and write protected RAM 314. Microprocessor 302 and RAM 312/314 cooperate with a number of processing modules to implement a methodology to control write access to protected RAM 314. These modules include address decoder module 304, accessories control registers module 306, fault detection module 308, and RAM interface module 310.

As was previously discussed, protected RAM 314 may be implemented as part of, or separate from, RAM 312. Also, it is understood that each of the processing modules 304, 306, 308, 310 may be implemented in hardware, software, or a combination of hardware and software. One or more of modules 304, 306, 308, 310 may further be embodied in a single IC device or in separate IC components and in accordance with a variety of packaging technologies. Further, one or more of modules 304, 306, 308, 310 may be implemented in software or hardware as part of microprocessor 302. In one embodiment, each of the four modules 304, 306, 308, 310 is implemented in integrated circuit form.

A write access methodology implemented by the system architecture 300 shown in FIG. 6 will be described with reference to four code-level examples provided hereinbelow. Each of the four code-level examples illustrate various operations performed by a corresponding one of the four processing modules 304, 306, 308, 310 shown in FIG. 6. The code-level examples are presented as RTL (Register Transfer Level) descriptions of the processing modules 304, 306, 308, 310 that cooperate with microprocessor 302 and RAM 312/314 to implement the write lock functionality according to the principles of the present invention.

Those skilled in the art will readily appreciate that RTL is a subset of Verilog® Hardware Description Language, manufactured by Cadence Design Systems, Inc., and that RTL descriptions are typically synthesized into logic gates using known software products and techniques. By way of example, the RTL examples provided below may be further processed by Design Compiler, version 1997.08, manufactured by Synopsys Corporation, to produce a gate level hardware implementation of write lock functionality.

The address decoder module 304 performs the general tasks of decoding global bus addresses and providing chip selections to a target module. An RTL code-level and memory map example of the address decoder module 304 implemented in accordance with one embodiment of the present in invention is provide below:

EXAMPLE #1

```
*    adrs_dec - global bus address decode
*
*    physical
*    address range   size   selected device
*    -------------   ----   ---------------
*    00000 - 03fff   16K    internal RAM (except for where registers
*                                         overlay memory)
*
*    00250 - 002ff   192    registers
*/
module adrs_dec
    active_bus_cycle,
    adrs,
    cs_iram,
    cs_acc_rgtrs,
input    active_bus_cycle;   // 1 => active bus cycle
                             // 0 => dummy bus cycle by microprocessor
input [19:0] adrs;    // bus address
output   cs_iram;    // 1 => select internal ram
output   cs_acc_rgtrs;   // 1 => select other accessories registers
// --- Address Decode ---
assign cs_acc_rgtrs = active_bus_cycle && (adrs >= 20'h0_0270)
                      && (adrs <= 20'h0_027f);
. . . assign cs_iram = (active_bus_cycle && (adrs >= 20'h0_0000)
                      && (adrs <= 20'h0_3fff) && !JTmem_test)
endmodule
```

The accessories control registers module 306 is written to by microprocessor 302, and stores the address range within RAM 312 that defines the protected or write locked RAM 314. Among other functions and outputs, accessories control registers module 306 produces two signals (ram_lock_upper and ram_lock_lower) that define the address range of protected RAM 314. The ram_lock_upper and ram_lock_lower signals are communicated to the fault detection module 308 for further processing. One embodiment of the accessories control registers module 306 is illustrated in the RTL example provided below:

EXAMPLE #2

```
*    acc_rgtrs - accessories control registers
*
*    The register map for the accessories control registers module is:
*
*    adrs    width    description
*    ---     -----    ------------------
*    4       8        Ramlock limits
*    e       8        Fault register
*/
module acc_rgtrs
    (reset,
    cs,
    rd,
    wr,
    adrs,
    wr_data,
    rd_data,
    ram_lock_upper,
    ram_lock_lower,
    porstat2,
    cs_porstat2,
    );
              //-- Bus Interface
. . . input    cs;     // 1 => current bus cycle is for memory mapped
. . . .                // registers
```

13
-continued

```
input      rd;         // 1 => read bus cycle
input      wr;         // 1 => write bus cycle - write on rising edge
                       //   of wr
input [3:0] adrs;      //
input [7:0] wr_data;   // data for a write cycle
output [7:0] rd_data;  // data from selected register on read cycle
           //-- RAM Lock
output [3:0] ram_lock_upper; // upper 1K write only page (in IRAM)
output [3:0] ram_lock_lower; // lower 1K write only page (in IRAM)
           //-- Fault Registers
input [7:0] porstat2;     // POR generating faults
output   cs_porstat2;     // 1 => fault register access (read or write)
// --- Internal Register Address Definitions
parameter RAM_LOCK = 4'h4;
parameter PORSTAT2 = 4'he;
// --- Register Definitions ---
reg [3:0] ram_lock_lower;
reg [3:0] ram_lock_upper;
// --- Internal Wire Definitions ---
wire wr_ram_lock;   // write ram lock register on falling edge
// RAM Lock
assign wr_ram_lock = cs && (adrs==RAM_LOCK) && wr;
always @(posedge reset or negedge wr_ram_lock) begin
   if (reset) begin
      ram_lock_lower = 4'hf;
      ram_lock_upper = 4'h0;
   end
   else begin
      ram_lock_lower = wr_data[3:0];
      ram_lock_upper = wr_data[7:4];
   end
end
// Fault register access signals
assign cs_porstat2 = cs && (adrs==PORSTAT2);
// --- Read Data Mux
assign rd_data =
   | {8{cs && rd && (adrs==PORSTAT2)}} & {  porstat2}
   endmodule
```

The fault detection module 308 detects memory addressing faults. A typical set of memory addressing faults are implicated upon the occurrence of a write to RAM 312/314 that has been locked as read only. A memory addressing fault typically causes a Power on Reset (POR) to be requested. A POR is a global request to all of the logic, including the microprocessor, in the system.

In general terms, the RAM lock mode is used to designate a block of memory in internal or external RAM as read only. As was stated previously, a primary motivation for providing the write lock functionality is to strictly limit access (i.e., lock) executable code stored in RAM 312/314 so as to prevent an errant program from corrupting itself, for example. The lower and upper bounds of the protected RAM 314 define the limits of the protected portion 314 of RAM 312. Additional RAM 312 memory space bounding the protected RAM portion 314 may also be considered part of protected RAM 314.

In the following example, it is assumed that the accessories control registers module 306 produces two signals, ram_lock_upper and ram_lock_lower, that define the address range of protected RAM 314. The ram_lock_upper and ram_lock_lower signals are communicated from accessories control registers module 306 to fault detection module 308. If a memory write falls within a 1K block greater than or equal to the value of ram_lock_lower and less than or equal to the value of ram_lock_upper, a memory fault is generated.

In order to disable the RAM lock capability, the value of ram_lock_upper may be set to a value less than that of ram_lock_lower. The RAM lock is generally applied to internal RAM, but may alternatively be implemented in external RAM.

14

If a fault occurs, the fault is latched in a fault status register and remains latched until the fault register is read. The fault status register is cleared on the cycle following the read, unless a fault occurs during that cycle, in which case the fault is latched in the fault status register. Faults occurring during the fault read cycle are generally not detected, but no faults can occur during this cycle, since this cycle is devoted to reading the fault status register. The fault status registers, which contain the fault indications, are not cleared on reset, so software can determine the POR cause.

An RTL code-level example of one implementation of a fault detection module 308 in accordance with the present invention is provided below:

EXAMPLE #3

```
* faultdet - memory addressing fault detection
module faultdet
   (mixed_clk,
   reset,
   ewr,
   cs_porstat2,
   adrs13_10,
   wrdata,
   cs_iram,
   ram_lock_lower,
   ram_lock_upper,
   match,
   porstat2,
   ram_lock_adr);
input       mixed_clk;   // microprocessor E clock or 32kHz clock
input       reset;       // 1 => reset
input       ewr;         // 1 => write (extended write)
input       cs_porstat2; // 1 => fault register access (rd or wr)
input [3:0] adrs13_10;   // bus address
input [7:0] wrdata;      // bus write data
input       cs_iram;     // 1 => select internal ram or registers
input [3:0] ram_lock_lower; // lower 1K boundary to be designated
                                read only
input [3:0] ram_lock_upper; // upper 1K boundary to be designated
                                read only
input       match;        // indicates that a pattern match occured
output [7:0] porstat2;    // consolidated fault register
output      ram_lock_adr; // RAM Lock Address selected
// --- Internal Register Definitions ---
wire   set_wr_lock;   // 1 => set ram lock fault
reg    reg_wr_lock;   // write to RAM that has been locked as read only
// --- Fault detection ---
assign ram_lock_adr = cs_iram & (adrs13_10 >= ram_lock_lower)
                            & (adrs13_10 <= ram_lock_upper);
// set fault bit only if a pattern match has not occurred
assign set_wr_lock = ewr && ram_lock_adr && !match;
// --- Fault register control ---
always @(posedge reset or posedge mixed_clk)
   if (reset)
      begin
         reg_wr_lock <= 1'b0;
      end
   else
      reg_wr_lock <= (reg_wr_lock & !(cs_porstat2 & ewr & (wrdata[2]
                           || wrdata[1]))) | set_wr_lock;
end
// --- Fault register ---
assign porstat2 = {0,0,0,0,0,0,0,reg_wr_lock};
endmodule
```

RAM interface module 310, in response to signals received from address control registers module 304 and microprocessor 302, generates a write signal to RAM 312 that provides write access to protected RAM 314. The output of RAM interface module 310 is an iram_wr signal that determines whether or not protected RAM 314 will actually be written. It is noted that in this embodiment, RAM interface module 310 is coupled to RAM 312/314 via a bidirectional data bus, and that conventional SRAM read and write pulses may be communicated over the data bus in a manner known in the art.

An RTL code-level example of one implementation of a RAM interface module 310 in accordance with the present invention is provided below:

EXAMPLE #4

```
module iram_interface
    (cs,
    wr,
    iram_wr,
        ram_lock_adr
    );
input    cs;         // 1 => iram selected for read or write
input    wr;         // 1 => write iram on rising edge of E if cs==1
output   iram_wr;    // 1 => write iram on rising edge of iram_wr
input    ram_lock_adr; // Locked RAM Address
// --- IRAM Read and Write Pulse Generation ---
assign iram_wr = (cs && wr && !ram_lock_adr);
endmodule
```

Override module 309 allows microprocessor 302 to override write lock protection for a predetermined amount of time after performing data matching typically by writing a predetermined value or data pattern to an unlock register. An RTL code-level example of one implementation of a RAM override module 309 in accordance with the present invention is provided below:

EXAMPLE #5

```
module overide (
                clk,
                cs,
                wr,
                reset,
                ram_lock_adr_in,
                adrs,
                wr_data,
                ram_lock_adr_out,
                match
                );
input      clk;          // clock input
input cs;                // module (chip) select input
input wr;                // write strobe
input reset;             // global reset (POR)
input ram_lock_adr_in;   // RAM lock address decode
input [3:0] adrs;        // address bus input
input [7:0] wr_data;     // write data input
output     ram_lock_adr_out; // RAM lock output
output     match;        // high if unlock register matches
                         // the pattern
                         // parameters
parameter  unlock = 4'h9;  // address of unlock register
parameter  pattern = 8'ha6; // pattern that must be matched
parameter  timeout = 8'h15; // timeout value after which the over
                            // ride of the write lock will be
                            // removed (writes no longer allowed)
                            // registers
reg [7:0]  reg_unlock;   // unlock register to which the pattern
                         // must be written
reg [7:0]  reg_count;    // counter for time out of over ride
                         // wires
wire time_out;           // high if timer has timed out
wire wr_unlock;          // high if unlock address is decoded
// decode address
assign wr_unlock = cs && wr && (adrs == unlock);
// unlock register
always @(posedge reset or posedge clk) begin
    if (reset) reg_unlock <= 8'h0;
    else if (wr_unlock) reg_unlock <= wr_data;
    else if (time_out) reg_unlock <= 8'h0;
end // always @ (posedge reset or posedge clk)
// pattern match
assign match = (reg_unlock == pattern);
// time out timer
always @(posedge reset or posedge clk) begin
    if (reset) reg_count <= 0;
    else if (timeout) reg_count <=0;
    else if (match) reg_count <= reg_count +1;
    else         reg_count <= 0;
end // always @ (posedge reset or posedge clk)
// time out decode
assign time_out = (reg_count == timeout);
// inhibit ram_lock_adr_out output if match is high
assign ram_lock_adr_out = ram_lock_adr_in && !match;
endmodule // overide
```

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use in conjunction with a particular type of programmable memory, such as volatile random access memory, but may be used in conjunction with memory devices fabricated using other technologies. Further, the present invention may be employed in a wide variety of processor-based implantable medical devices, and may further be implemented in low power applications other than in implantable medical devices. The present invention is also not limited to specific memory addressing and control techniques, such as those presented herein, but such functions may be directed using other like techniques. The present invention further includes within its scope methods of using the programmable memory protection apparatus as well as the structural particulars described hereinabove.

In the claims, means plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A body implantable medical apparatus, comprising:

a hermetically sealed housing;

a random access memory (RAM) disposed in the housing;

a write protected RAM portion defined as part of the RAM;

a microprocessor disposed in the housing and coupled to the RAM, the microprocessor generating an access code for providing write access to the write protected RAM portion; and a logic circuit, disposed in the housing and coupled to the RAM and microprocessor, that verifies the access code received from the microprocessor, the logic circuit enabling write access to the write protected RAM portion in response to a verified access code and disabling write access to the write protected RAM portion in response to an unverified access code.

2. The apparatus of claim 1, wherein executable software is stored in the write protected RAM portion, the executable software including program code executed by the microprocessor to control operations of the implantable medical apparatus.

3. The apparatus of claim 2, wherein the logic circuit enables write access to alter the executable software stored in the write protected RAM portion in response to the verified access code, and prevents alteration of the executable software by disabling write access to the write protected RAM portion in response to the unverified access code.

4. The apparatus of claim 1, wherein the logic circuit comprises a verification register for receiving the access code generated by the microprocessor.

5. The apparatus of claim 1, wherein:
the access code comprises data having a pre-established pattern; and
the logic circuit comprises a verification register that receives the access code and verifies that the access code data conforms to the pre-established pattern.

6. The apparatus of claim 1, further comprising a timer circuit coupled to the logic circuit, the timer circuit transmitting, in response to expiration of a pre-established timeout period, a reset signal to the logic circuit to disable write access to the write protected RAM portion.

7. The apparatus of claim 1, wherein the microprocessor establishes the write protected RAM portion as a contiguous block of RAM addresses.

8. The apparatus of claim 1, wherein, in response to a loss of power, the logic circuit generates a power on reset signal to disable write access to the write protected RAM portion upon reestablishing the power.

9. The apparatus of claim 1, wherein the RAM comprises static RAM, dynamic RAM, or electrically erasable programmable read only memory.

10. An apparatus for protecting memory content, comprising:
a random access memory (RAM);
a write protected RAM portion defined as part of the RAM;
a microprocessor coupled to the RAM, the microprocessor generating an access code for providing write access to the write protected RAM portion; and
a logic circuit, coupled to the RAM and microprocessor, that verifies the access code received from the microprocessor, the logic circuit enabling write access to the write protected RAM portion in response to a verified access code and disabling write access to the write protected RAM portion in response to an unverified access code.

11. The apparatus of claim 10, wherein executable software is stored in the write protected RAM portion.

12. The apparatus of claim 11, wherein the logic circuit enables write access to alter the executable software stored in the write protected RAM portion in response to the verified access code, and prevents alteration of the executable software by disabling write access to the write protected RAM portion in response to the unverified access code.

13. The apparatus of claim 10, wherein the logic circuit comprises a verification register for receiving the access code generated by the microprocessor.

14. The apparatus of claim 10, wherein:
the access code comprises data having a pre-established pattern; and
the logic circuit comprises a verification register that receives the access code and verifies that the access code data conforms to the pre-established pattern.

15. The apparatus of claim 10, further comprising a timer circuit coupled to the logic circuit, the timer circuit transmitting, in response to expiration of a pre-established timeout period, a reset signal to the logic circuit to disable write access to the write protected RAM portion.

16. The apparatus of claim 10, wherein the microprocessor establishes the write protected RAM portion comprising an upper bound address and a lower bound address, the logic circuit generating a memory fault signal in response to attempted write access to the write protected RAM portion in an absence of the verified access code.

17. The apparatus of claim 10, wherein the microprocessor establishes the write protected RAM portion as a contiguous block of RAM addresses.

18. The apparatus of claim 10, wherein the microprocessor establishes the write protected RAM portion as a plurality of RAM addresses defined within a first 16K bytes of physical memory of the RAM.

19. The apparatus of claim 10, wherein, in response to a loss of power, the logic circuit generates a power on reset signal to disable write access to the write protected RAM portion upon reestablishing the power.

20. The apparatus of claim 10, wherein the RAM comprises static RAM, dynamic RAM, or electrically erasable programmable read only memory.

21. A method of protecting contents of a random access memory (RAM) coupled to a microprocessor; comprising
establishing a protected portion of the RAM for storing executable software;
generating an access code for providing write access to the protected portion of the RAM;
verifying the access code prior to providing write access to the protected portion of the RAM;
preventing write access to the protected portion of the RAM in response to an unverified access code; and
providing write access to the protected portion of the RAM in response to a verified access code.

22. The method of claim 21, wherein establishing the protected portion of the RAM comprises designating a plurality of RAM storage locations to define the protected portion of the RAM.

23. The method of claim 21, wherein establishing the protected portion of the RAM comprises designating a range of RAM addresses to define the protected portion of the RAM.

24. The method of claim 23, wherein designating the range of RAM addresses comprises designating a contiguous block of RAM addresses to define the protected portion of the RAM.

25. The method of claim 21, wherein:
generating the access code comprises generating data having a pre-established pattern; and
verifying the access code comprises verifying that the data conforms to the pre-established pattern.

26. The method of claim 21, wherein generating the access code comprises generating data having a pre-established pattern, and verifying the access code comprises:
writing the access code to a verification register coupled to the microprocessor; and
verifying that the data associated with the access code received by the verification register conforms to the pre-established pattern.

27. The method of claim 21, wherein preventing write access to the protected portion of the RAM comprises disabling a write signal produced by the microprocessor in response to the unverified access code.

28. The method of claim 21, wherein providing write access to the protected portion of the RAM comprises enabling a write signal produced by the microprocessor in response to the verified access code.

29. The method of claim 21, wherein providing write access comprises providing write access to the protected portion of the RAM for a predetermined duration of time.

30. An apparatus for protecting contents of a random access memory (RAM) coupled to a microprocessor; comprising means for generating an access signal for providing write access to a protected portion of the RAM, the protected portion of the RAM storing executable software;

means for verifying the access signal prior to providing write access to the protected portion of the RAM;

means for preventing write access to the protected portion of the RAM in response to an unverified access signal; and means for providing write access to the protected portion of the RAM in response to a verified access signal.

31. The apparatus of claim 30, further comprising means for establishing the protected portion of the RAM.

32. The apparatus of claim 30, wherein the generating means comprises means for generating a verification signal having a pre-established pattern; and the verifying means comprises means for verifying that the access signal conforms to the pre-established pattern of the verification signal.

33. The apparatus of claim 30, wherein the generating means comprises means for generating a verification signal having a pre-established pattern, and the verifying means comprises:

means for writing the access signal to a verification register coupled to the microprocessor; and means for verifying that the access signal received by the verification register conforms to the pre-established pattern of the verification signal.

34. The apparatus of claim 30, wherein the preventing means comprises means for disabling a write signal produced by the microprocessor in response to the unverified access signal.

35. The apparatus of claim 30, wherein the providing means comprises means for enabling a write signal produced by the microprocessor in response to the verified access signal.

36. The apparatus of claim 30, wherein the providing means comprises means for providing write access to the protected portion of the RAM for a predetermined duration of time.

* * * * *